United States Patent
Horner et al.

(10) Patent No.: US 8,439,913 B2
(45) Date of Patent: May 14, 2013

(54) PRESSURE SENSING SEALING PLATE

(75) Inventors: Glenn A. Horner, Boulder, CO (US); Christina A. Oliver, Longmont, CO (US); Kim V. Brandt, Loveland, CO (US)

(73) Assignee: Covidien LP, Mansfield, MA (US)

( * ) Notice: Subject to any disclaimer, the term of this patent is extended or adjusted under 35 U.S.C. 154(b) by 476 days.

(21) Appl. No.: 12/770,369

(22) Filed: Apr. 29, 2010

(65) Prior Publication Data
US 2011/0270252 A1 Nov. 3, 2011

(51) Int. Cl.
*A61B 18/14* (2006.01)

(52) U.S. Cl.
USPC .................................. 606/52; 606/51; 606/45

(58) Field of Classification Search ............... 606/45–52
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D348,930 S | 7/1994 | Olson |
| D384,413 S | 9/1997 | Zlock et al. |
| 6,017,354 A | 1/2000 | Culp et al. |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| D493,888 S | 8/2004 | Reschke |
| D496,997 S | 10/2004 | Dycus et al. |
| D499,181 S | 11/2004 | Dycus et al. |
| D509,297 S | 9/2005 | Wells |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,235,072 B2 * | 6/2007 | Sartor et al. .................... 606/45 |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Linda Dvorak
*Assistant Examiner* — Amanda Scott

(57) ABSTRACT

An end effector assembly for use with an electrosurgical instrument is provided. The end effector assembly has a pair of opposing jaw members. One or more of the jaw members includes a support base, an electrical jaw lead, and a sealing plate coupled to the electrical jaw lead. The sealing plate has a stainless steel layer and one or more piezoelectric sensors. The jaw member also includes an insulative plate disposed between the support base and the sealing plate.

6 Claims, 7 Drawing Sheets

U.S. PATENT DOCUMENTS

| | | | |
|---|---|---|---|
| 7,491,202 B2* | 2/2009 | Odom et al. ............... | 606/51 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,963,963 B2* | 6/2011 | Francischelli et al. ...... | 606/51 |
| 8,112,871 B2* | 2/2012 | Brandt et al. ............... | 29/592.1 |
| 2004/0230262 A1* | 11/2004 | Sartor et al. ............... | 607/96 |
| 2006/0224158 A1* | 10/2006 | Odom et al. ............... | 606/51 |
| 2007/0062017 A1 | 3/2007 | Dycus | |
| 2008/0319442 A1 | 12/2008 | Unger | |
| 2009/0204114 A1 | 8/2009 | Odom | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| EP | 1707143 | 10/2006 |
| EP | 1946715 | 7/2008 |
| EP | 1990019 | 11/2008 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2004/073753 | 9/2004 |
| WO | WO 2005/110264 | 11/2005 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/762,482, filed Apr. 19, 2010.
U.S. Appl. No. 12/766,476, filed Apr. 23, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.

Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11164274 dated Aug. 3, 2011.

* cited by examiner

PRESSURE SENSING SEALING PLATE

BACKGROUND

1. Technical Field

The present disclosure relates to an electrosurgical instrument and method for sealing tissue. More particularly, the present disclosure relates to an electrosurgical tool including opposing jaw members having pressure sensors for determining a seal pressure and controlling operation of the electrosurgical tool based on the determined seal pressure.

2. Background of the Related Art

Electrosurgical forceps utilize mechanical clamping action along with electrical energy to effect hemostasis on the clamped tissue. The forceps (open, laparoscopic or endoscopic) include electrosurgical sealing plates which apply the electrosurgical energy to the clamped tissue. By controlling the intensity, frequency and duration of the electrosurgical energy applied through the sealing plates to the tissue, the surgeon can coagulate, cauterize, and/or seal tissue.

Since tissue sealing procedures involve more than simply cauterizing tissue and blood, to create an effective seal the procedures involve precise control of a variety of factors. In order to affect a proper seal in vessels or tissue, it has been determined that two predominant mechanical parameters should be accurately controlled: the pressure applied to the tissue; and the gap distance between the electrodes (i.e., distance between opposing jaw members when closed about tissue).

Numerous electrosurgical instruments have been proposed in the past for various endoscopic surgical procedures. However, most of these instruments cauterize or coagulate tissue and do not allow the sufficiently strong tissue fusion of all tissue types. Consequentially, many of the existing instruments generally rely on clamping pressure alone to procure proper sealing thickness and are often not designed to take into account the seal pressure and applying energy to seal the tissue either sinusoidally or based on feedback from the tissue or properties of the device.

SUMMARY

In an embodiment of the present disclosure, an end effector assembly including a pair of opposing jaw members is provided. One or more of the jaw members includes a support base, an electrical jaw lead, and a sealing plate coupled to the electrical jaw lead. The sealing plate has a stainless steel layer and one or more piezoelectric sensors. The jaw member also includes an insulative plate disposed between the support base and the sealing plate.

The insulative plate is a flex circuit having a plastic substrate and a circuit trace having one or more contacts coupled thereto. The one or more contacts are coupled to one or more piezoelectric sensors. The contact may be operatively coupled to a controller via a contact trace.

In another embodiment of the present disclosure, an electrosurgical instrument for sealing tissue is provided. The electrosurgical instrument may include a housing having at least one shaft that extends therefrom, a handle assembly operably coupled to the housing, a rotating assembly operably coupled to and configured to rotate the at least one shaft and an end effector assembly disposed at a distal end of the at least one shaft including a pair of opposing jaw members. One or more of the jaw members includes a support base, an electrical jaw lead, and a sealing plate coupled to the electrical jaw lead. The sealing plate has a stainless steel layer and one or more piezoelectric sensors. The jaw member also includes an insulative plate disposed between the support base and the sealing plate.

The insulative plate is a flex circuit having a plastic substrate and a circuit trace having one or more contacts coupled thereto. The one or more contacts are coupled to one or more piezoelectric sensors. The contact may be operatively coupled to a controller via a contact trace.

In yet another embodiment, a method of constructing a jaw member for an end effector assembly is provided. The method includes creating a seal plate by shaping a stainless steel layer into a seal plate, applying a first mask to the stainless steel layer, wherein the first mask exposes a portion of the stainless steel layer, etching the exposed portion of stainless steel layer to create one or more holes in the stainless steel layer and removing the mask. An insulative plate is also created by providing a plastic substrate, adhering a conductive layer to the plastic substrate, applying a second mask to the conductive layer, wherein the second mask exposes a portion of the conductive layer to outline one or more circuit traces and one or more contacts, etching the exposed portion of the conductive layer, and removing the mask. A support base is provided and the insulative plate is attached to the support base and the seal plate is attached on top of the insulative plate so that the one or more holes of the seal plate overlaps the one or more contacts of the insulative plate. A piezoelectric sensor is coupled to the at least one contact of the insulative plate. The piezoelectric sensor is disposed in the one or more holes of the seal plate.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
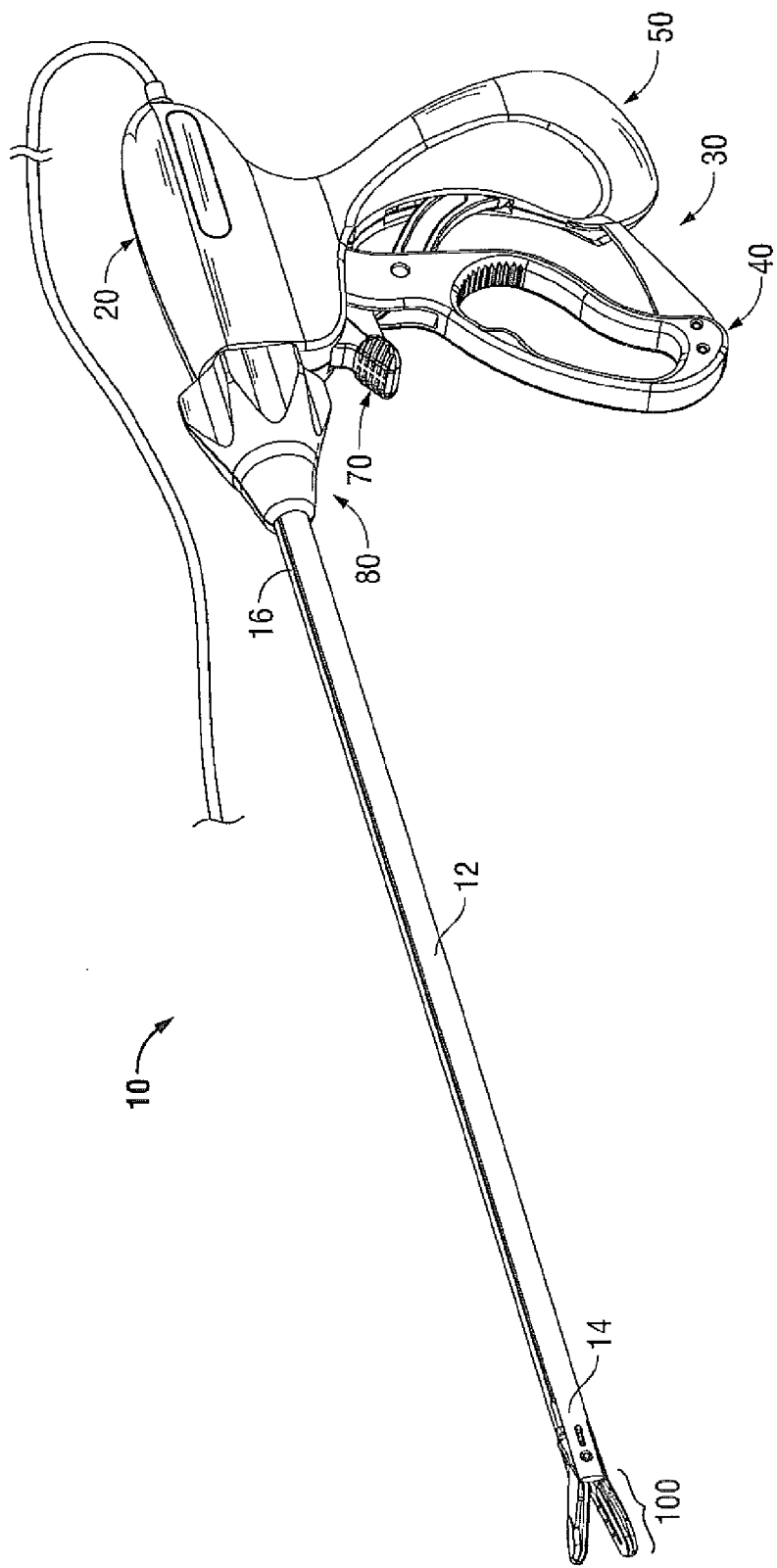
FIG. 1 is a perspective view of an endoscopic bipolar forceps in accordance with an embodiment of the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of embodiments described herein.

As described in more detail below with reference to the accompanying figures, the present disclosure is directed the use of piezoelectric sensors in a vessel sealing procedure. More specifically, piezoelectric sensors are used instead of conventional ceramic stop members. The piezoelectric sensors provide a seal pressure to a controller that adjusts the closure pressure of the jaw members according to open loop or closed loop feedback mechanisms. By using piezoelectric sensors instead of stop members, jaw members may be made smaller as well as provide better controlled sealing of certain tissue types or new tissue types.

Turning to FIG. 1, an instrument generally identified as forceps 10 is for use with various surgical procedures and includes a housing 20, a handle assembly 30, a rotating assembly 80, a trigger assembly 70, and an end effector assembly 100 that mutually cooperate to grasp, seal, and divide tubular vessels and vascular tissues. Forceps 10 includes a shaft 12 that has a distal end 16 dimensioned to mechanically engage the end effector assembly 100 and a proximal end 14 that mechanically engages the housing 20. The end effector assembly 100 includes opposing jaw members 110 and 120, which cooperate to effectively grasp tissue for sealing purposes. The end effector assembly 100 is a bilateral assembly, i.e., both jaw members 110 and 120 pivot relative to one another about a pivot pin 95. Unilateral jaw assemblies may also be contemplated. The jaw members 110 and 120 are curved to facilitate manipulation of tissue and to provide better "line of sight" for accessing targeted tissues.

Examples of forceps are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 (now U.S. Pat. No. 7,156, 846) entitled "VESSEL SEALER AND DIVIDER FOR USE WITH SMALL TROCARS AND CANNULAS.

Figure 2:
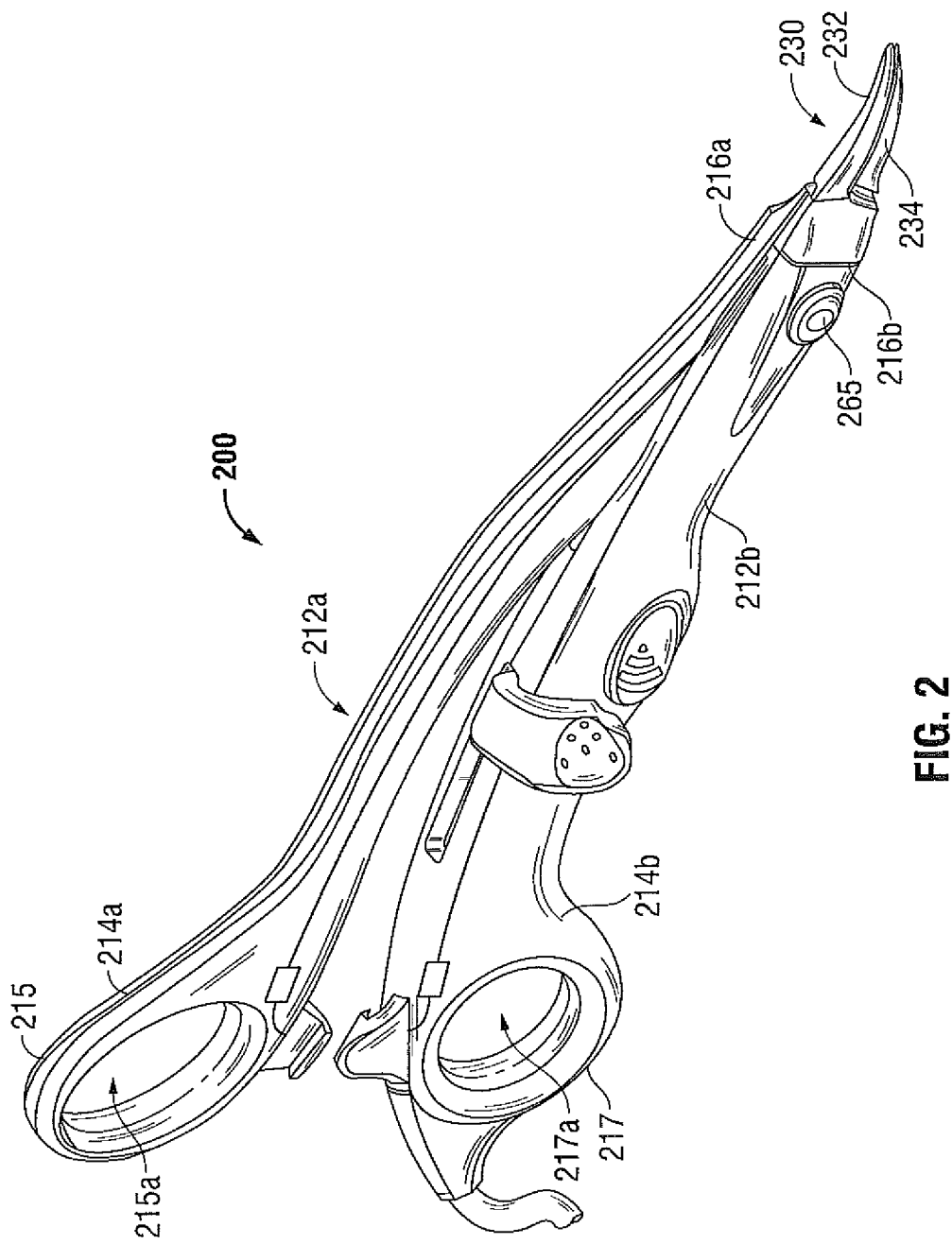
FIG. 2 is a perspective view of an open bipolar forceps in accordance with an embodiment of the present disclosure.

With regard to FIG. 2, an open forceps 200 for use with various surgical procedures is shown. Forceps 200 includes a pair of opposing shafts 212a and 212b having an end effector assembly 230 attached to the distal ends 216a and 216b thereof, respectively. End effector assembly 230 is similar in design to end effector assembly 100 and includes pair of opposing jaw members 232 and 234 that are pivotably connected about a pivot pin 265 and which are movable relative to one another to grasp tissue. Each shaft 212a and 212b includes a handle 215 and 217, respectively, disposed at the proximal end 214a and 214b thereof which each define a finger hole 215a and 217a, respectively, therethrough for receiving a finger of the user. Finger holes 215a and 217a facilitate movement of the shafts 212a and 212b relative to one another which, in turn, pivot the jaw members 232 and 234 from an open position wherein the jaw members 232 and 234 are disposed in spaced relation relative to one another to a clamping or closed position wherein the jaw members 232 and 234 cooperate to grasp tissue therebetween.

Figure 3A:
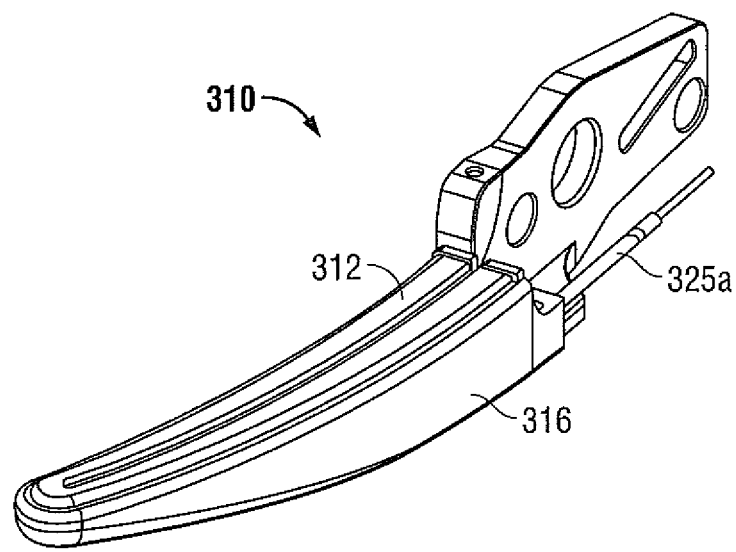
FIGS. 3A and 3B are perspective views of opposing jaw members according to an embodiment of the present disclosure.
Figure 3B:
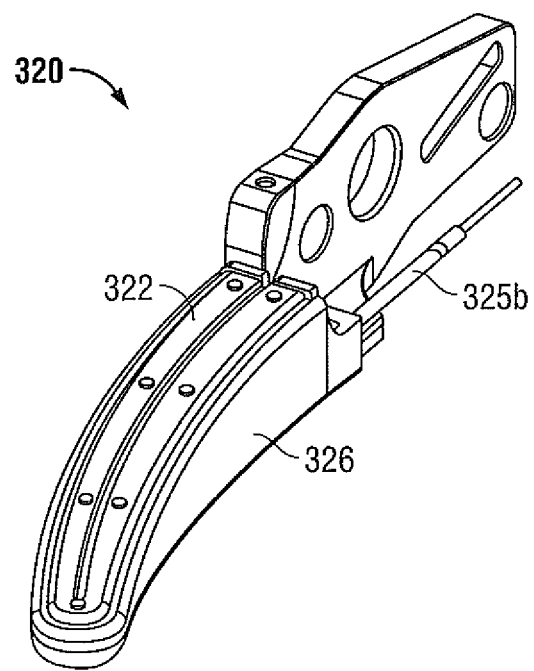

FIGS. 3A and 3B are perspective views of the opposing jaw members 310 and 320. Similar to jaw members 110 and 120, each of the jaw members 310 and 320 include: sealing plates 312 and 322, respectively; electrical jaw leads 325a and 325b, respectively; and support bases 316 and 326 formed as plastic overmolds. Electrical jaw leads 325a and 325b supply energy to at least one of the opposing jaw members 310 and 320.

Figure 4A:
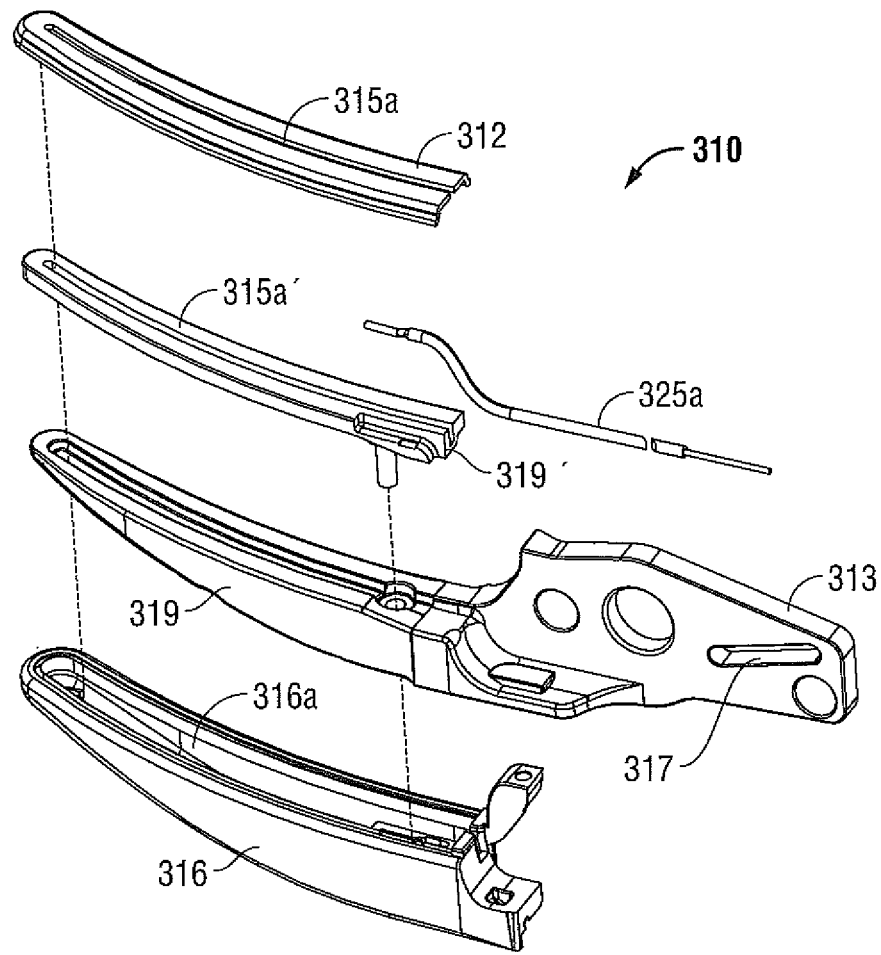
FIGS. 4A and 4B are exploded views of the opposing jaw members of FIGS. 3A and 3B respectively.
Figure 4B:
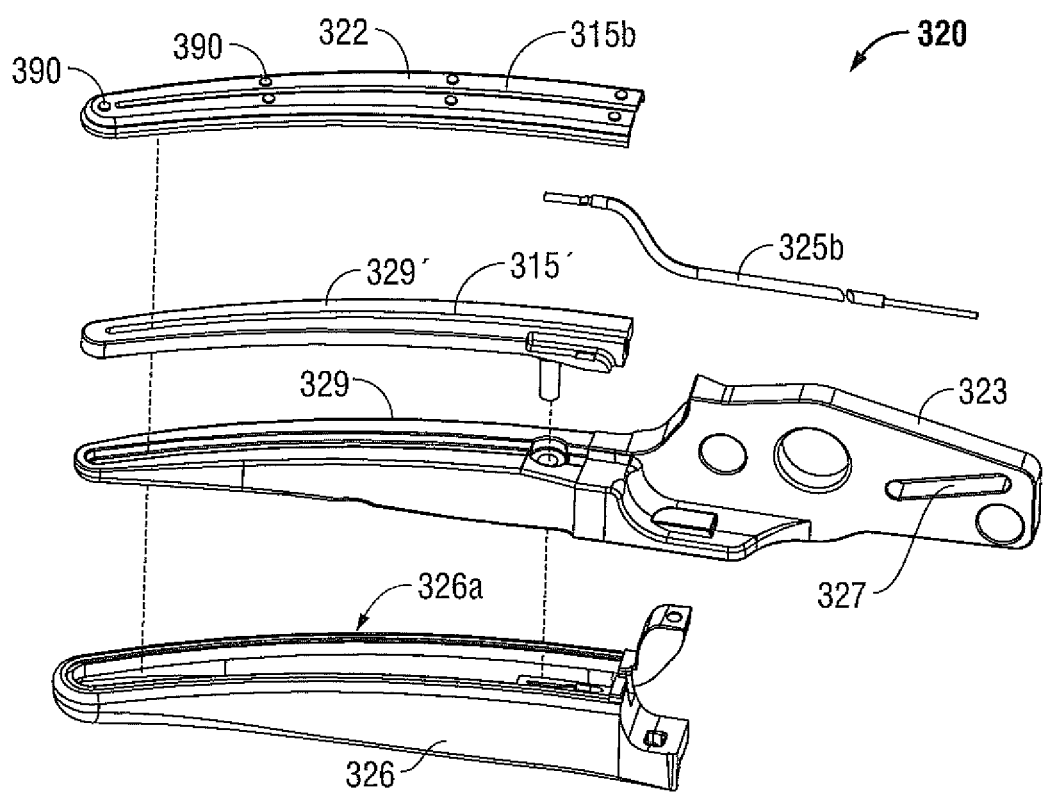

Turning to FIGS. 4A and 4B, the opposing jaw members 310 and 320 include support bases 316 and 326 that each extend distally from flanges 313 and 323, respectively. The support bases 316 and 326 are dimensioned to support insulative plates 319' and 329', which in turn, support electrically conductive sealing plates 312 and 322 thereon. It is contemplated that sealing plates 312 and 322 may be affixed atop the insulative plates 319' and 329', respectively, and support bases 319 and 329, respectively, in any known manner in the art, snap-fit, over-molding, stamping, ultrasonically welded, etc. The support bases 319 and 329, insulative plates 319' and 329', and sealing plates 312 and 322 are encapsulated by the outer insulative housings 316 and 326 by way of a subsequent overmolding process. The jaw members 310 and 320 are connected via an ultrasonic weld to electrical jaw leads 325a and 325b, respectively.

The jaw members 310 and 320 also include proximal flanges 313 and 323 extending proximally from the support bases 319 and 329, respectively, each of which includes an elongated angled cam slot 317 and 327, respectively, defined therethrough. The jaw member 320 also includes a series of piezoelectric sensors 390 disposed on the inner facing surface of an electrically conductive sealing plate 312 to define a gap between opposing sealing surfaces during sealing and cutting of tissue. In one embodiment, the gap is between about 0.001" and 0.006"; however, other suitable gaps are contemplated by the present disclosure. The series of piezoelectric sensors 390 are applied onto the sealing plate 312 during manufacturing. The electrically conductive sealing plates 312 and 322 and the insulative plates 319' and 329' include respective longitudinally-oriented knife slots 315a, 315a' and 315b, 315b', respectively, defined therethrough for reciprocation of the knife blade (not shown).

Figure 5A:
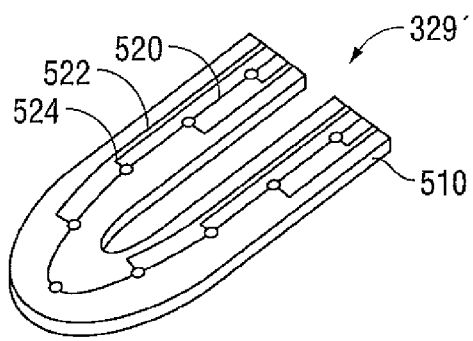
FIG. 5A is a top view of a insulation plate according to an embodiment of the present disclosure.

Turning to FIG. 5A, a top view of insulative plate 329' is shown. Insulative plate 329' is a flex circuit. Flex circuits are used to assemble electronic circuits by mounting electronic devices on flexible plastic substrates. Such plastic substrates may include, but are not limited to, polyimide or polyether ether ketone (PEEK) film. Flex circuits may also be constructed by screen printing silver or copper circuits onto polyester. As shown in FIG. 5A insulative plate 329' has a substrate 510 having circuit traces 520 formed thereon. Circuit traces 520 may be made from copper, silver, or any other electrical conductor. Circuit traces 520 may be formed by any suitable method. For instance, circuit traces 520 may be formed by adhering a conductive layer to substrate 510. Using photolithography, a mask outlining circuit traces 520 may be formed and then the conductive layer may be etched to leave circuit traces 520.

Circuit traces 520 include contacts 524 that may be made from copper, silver or any other suitable electrical conductor. Contacts 524 may be made from the same material as circuit traces 520 or from a material different from circuit traces 520. Each contact 524 is operatively coupled to controller 620 (FIG. 6) via contact traces 522. Contacts 524 and contact traces 522 are formed using the same techniques that may be used to form circuit traces 524. The location of contacts 524 correspond to the location of piezoelectric sensors 390.

Accordingly, when piezoelectric sensors 390 determine a seal pressure, piezoelectric sensors 390 provide a signal to controller 620 indicative of the seal pressure via contacts 524 and contact traces 522.

Figure 5B:
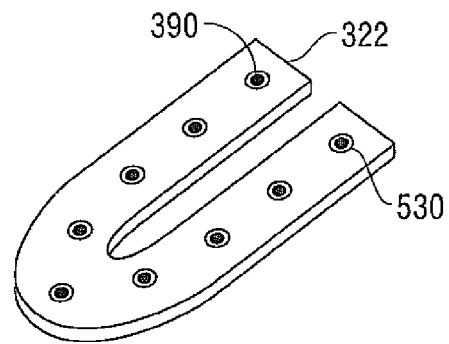
FIG. 5B is a top view of a sealing plate according to an embodiment of the present disclosure.

FIG. 5B depicts a top view of seal plate 322. Seal plate 322 is made from stainless steel, and as described above, has piezoelectric sensors 390 disposed therein in locations 530. Seal plate 322 may be formed by any suitable method. For instance, a layer of stainless steel may be provided and shaped to form seal plate 322. Then, a photolithography mask is applied to seal plate 322 leaving locations 530 exposed. An etching solution is applied to seal plate 322 to etch away exposed locations 530. Then the mask is removed leaving seal plate 322 with locations 530 etched away. When jaw member 320 is assembled, piezoelectric sensors 390 are placed in locations 530 of seal plate 322 and are coupled to contacts 524 of insulative plate 329'. Locations 530 may also be formed from other suitable methods, such as punching, drilling, etc.

Figure 6:
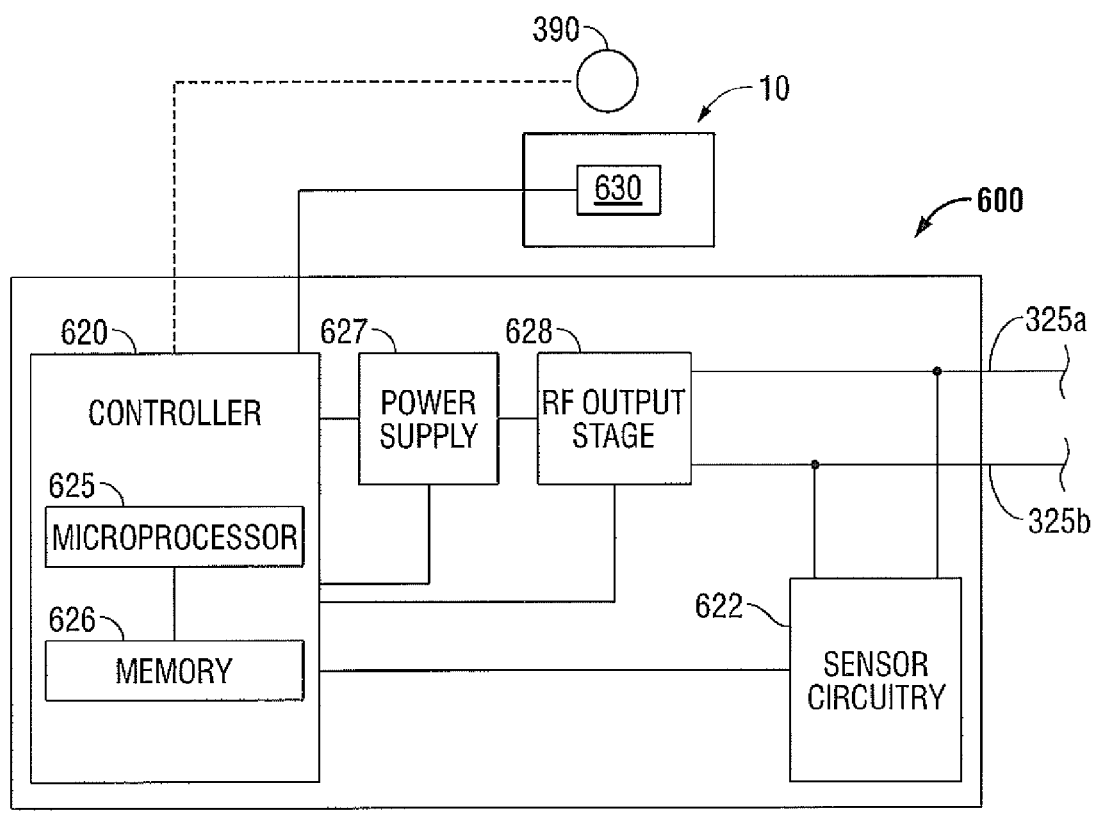
FIG. 6 is a schematic block diagram of an electrosurgical system according to an embodiment of the present disclosure.

FIG. 6 shows a schematic block diagram of the generator 600 having a controller 620, a power supply 627, an RF output stage 628, and a sensor module 622. The power supply 627 provides DC power to the RF output stage 628 which then converts the DC power into RF energy and delivers the RF energy to the instrument 10. The controller 620 includes a microprocessor 625 having a memory 626 which may be volatile type memory (e.g., RAM) and/or non-volatile type memory (e.g., flash media, disk media, etc.). The microprocessor 625 includes an output port connected to the power supply 627 and/or RF output stage 628 that allows the microprocessor 625 to control the output of the generator 600 according to either open and/or closed control loop schemes.

A closed loop control scheme generally includes a feedback control loop wherein the sensor module 622 provides feedback to the controller 24 (e.g., information obtained from one or more sensing mechanisms for sensing various tissue parameters such as tissue impedance, tissue temperature, output current and/or voltage, etc.). The controller 620 then signals the power supply 627 and/or RF output stage 628 which then adjusts the DC and/or RF power supply, respectively. The controller 620 also receives input signals from the input controls of the generator 600 and/or instrument 10. The controller 620 utilizes the input signals to adjust the power output of the generator 600 and/or instructs the generator 20 to perform other control functions.

The microprocessor 625 is capable of executing software instructions for processing data received by the sensor module 622, and for outputting control signals to the generator 600, accordingly. The software instructions, which are executable by the controller 620, are stored in the memory 626 of the controller 620.

The controller 620 may include analog and/or logic circuitry for processing the sensed values and determining the control signals that are sent to the generator 600, rather than, or in combination with, the microprocessor 625.

The sensor module 622 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 620. The sensor module 622 may include control circuitry that receives information from multiple sensors, and provides the information and the source of the information (e.g., the particular sensor providing the information) to the controller 620.

More particularly, the sensor module 622 may include a real-time voltage sensing system (not explicitly shown) and a real-time current sensing system (not explicitly shown) for sensing real-time values related to applied voltage and current at the surgical site. Additionally, an RMS voltage sensing system (not explicitly shown) and an RMS current sensing system (not explicitly shown) may be included for sensing and deriving RMS values for applied voltage and current at the surgical site.

The generator 600 includes suitable input controls (e.g., buttons, activators, switches, touch screen, etc.) for controlling the generator 600, as well as one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., tissue ablation). Further, the instrument 10 may include a plurality of input controls which may be redundant with certain input controls of the generator 600. Placing the input controls at the instrument 10 allows for easier and faster modification of RE energy parameters during the surgical procedure without requiring interaction with the generator 600.

A generator 600 according to the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Piezoelectric sensors 390 are configured to automatically sense the sealing pressure on the tissue disposed between the jaw members 110 and 120 and provide feedback to controller 620 during the sealing process. Controller 620 may then regulate and adjust the closure pressure between the jaw members 110 and 120 during the sealing process to enhance the tissue seal.

As seen in FIG. 6, piezoelectric sensors 390 may be coupled to the control assembly via an open loop or closed loop feedback system to regulate the seal pressure on the tissue between the jaw members 110 and 120. It is important to note that the closure pressure of the jaw members 110 and 120 correlates to, but is not necessarily the same as, the sealing pressure on the tissue disposed between the jaw members 110 and 120. The piezoelectric sensors 390 measure the sealing pressure on the tissue and relay the sealing pressure information back to controller 620 which operatively communicates with instrument 10 to adjust the sealing pressure based upon the information provided by piezoelectric sensors 390 and the desired sealing pressure according to a predetermined seal pressure profile.

Instrument 10 may include a pressure controller 630 that is operatively coupled to the shaft 12 of the forceps 10. The pressure controller 630 may be any type of electrical, or electro-mechanical mechanism that adjusts the force on the drive assembly (not shown) to increase or decrease the closure pressure of the jaw members 110 and 120 which, in turn, increases or decreases the seal pressure on the tissue disposed therebetween. For example, a servo motor, gear assembly, hydraulic mechanism, worm drive, etc. may be coupled to the shaft 12 and operatively coupled to the drive assembly (not shown) to provide additional force to the drive assembly (not shown) as per the information.

As mentioned above, in one embodiment, the initial closure pressure between the jaw members 110 and 120 upon actuation of the handle assembly 30 and locking of the moveable handle 40 relative to the fixed handle 50 is about 3 kg/cm² to about 16 kg/cm². The sealing pressure on the tissue may or may not fall within this range. The piezoelectric sensors 390 may be configured to initially determine the sealing pressure on tissue prior to initial activation of the forceps. For example, the piezoelectric sensors 390 may determine that additional force needs to be provided to the drive assembly (not shown) to increase the closure pressure of the jaw members 110 and 120 which, in turn, increases the sealing pressure of the tissue 400.

The appropriate sealing pressure for initial activation may be based upon a predetermined pressure profile stored within memory 626, which may be based on tissue type, tissue temperature, tissue size, etc. If more or less sealing pressure on tissue is required, controller 620 communicates with the pressure controller 630 to regulate the closure force of the jaw members 110 and 120. For example, while the handle 40 is locked relative to fixed handle 50, the pressure controller may be configured to provide +/−10 kg/cm² when required to match a predetermined pressure profile or pressure algorithm.

During the sealing process, the piezoelectric sensors 390, controller 620 and the pressure controller 630 all cooperate to regulate the sealing pressure on tissue to conform to a predetermined pressure profile or pressure algorithm. For example, the pressure controller 630 may be instructed by controller 620 to increase the closure pressure on the jaw members 110 and 120 (which increases the sealing pressure on tissue 400) due to the tissue shrinking during the sealing process. Moreover, the seal pressure may be cycled during electrical activation based upon a predetermined sinusoidal pressure profile to enhance the tissue seal. The piezoelectric sensors 390 may interact sequentially, simultaneously or in another manner to sense feedback from the tissue and determine the sealing pressure.

The procedure may be automated using a series of piezoelectric sensors 390, controller 620 and pressure controller 630. The sealing pressure control system described herein is believed to provide more effective sealing of tissue especially large tissue structures, such as lung tissue. In the automated system, the sealing pressure on the tissue is monitored and adjusted during activation based upon a continually-sensed surgical condition from the piezoelectric sensors 390 utilizing an open or closed feed back control loop. The pressure controller 630 may be manual, where the gauge instructs a user through a visual or audible indicator to increase or decrease the closure pressure on the jaw to in turn adjust the sealing pressure on the tissue.

Figure 7:
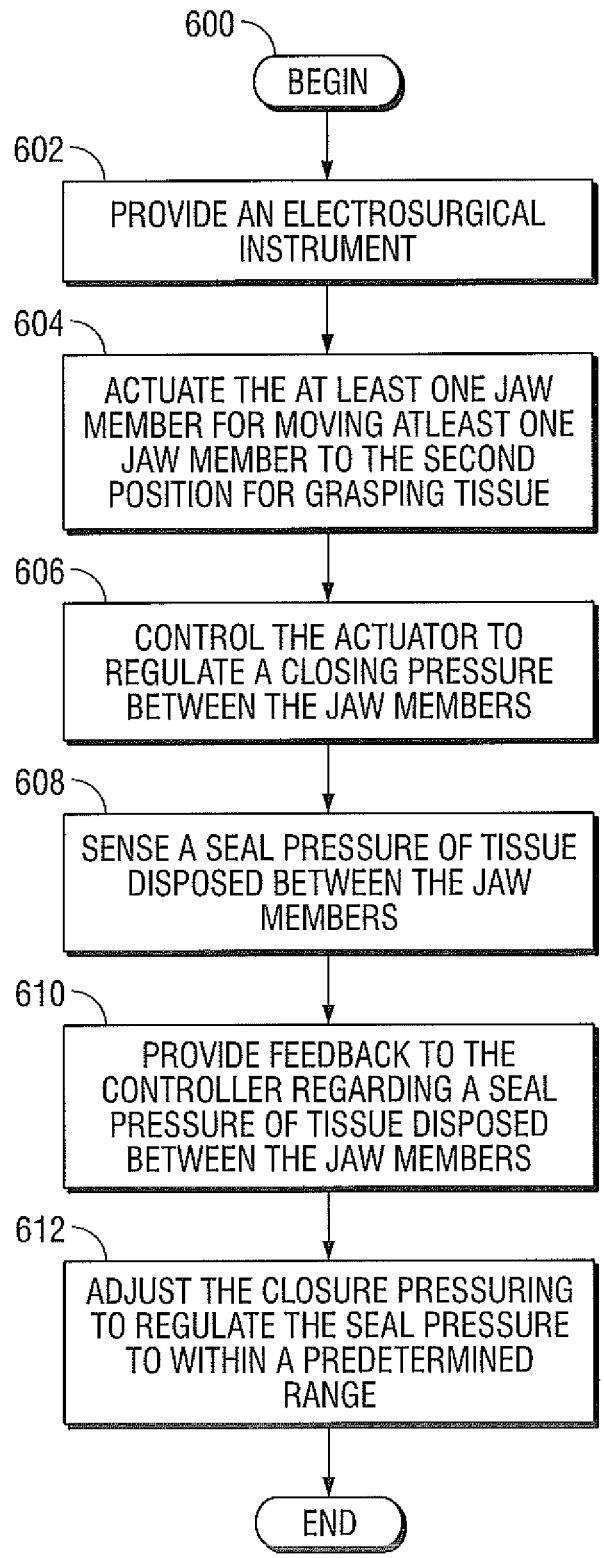
FIG. 7 is a flowchart depicting a sealing method using an electrosurgical instrument.

As shown in FIG. 7, a method for sealing tissue using the forceps 10 is also disclosed herein that includes the initial step 602 of providing an electrosurgical instrument, e.g., forceps 10, including one or more shafts 12 having an end effector assembly 100 at a distal end thereof, the end effector assembly 100 including a pair of opposing jaw members 110 and 120 movable from a first spaced apart position to a second position for grasping tissue. At least one jaw member, e.g., 110 is adapted to connect to an electrical energy source. In step 604, at least one jaw member 110 is actuated to the second position for grasping tissue. The closing pressure between the jaw members is regulated by controlling the actuator in step 606. The instrument 10 senses a seal pressure of tissue 400 disposed between the jaw members 110 and 120 in step 608 and provides feedback to controller 620 regarding the seal pressure of tissue disposed between the jaw members 110 and 120. In step 612, the pressure controller 630 adjusts the closing pressure to regulate the seal pressure of the jaw members 110 and 120 on the tissue during the sealing process to within a predetermined range.

In one method, the seal pressure may be determined prior to initial activation of the forceps, continually-sensed during the sealing process and/or after activation to determine seal quality. The seal pressure may be regulated according to a seal pressure profile (e.g., sinusoidal) or seal pressure algorithm. Moreover, the seal pressure may be cycled during electrical activation based upon a predetermined pressure profile or pressure algorithm.

The foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached figures are presented only to demonstrate certain examples of the disclosure. Other elements, steps, methods and techniques that are insubstantially different from those described above and/or in the appended claims are also intended to be within the scope of the disclosure.

What is claimed is:

1. An end effector assembly including a pair of opposing jaw members, at least one of the jaw members comprising:
   a support base;
   an electrical jaw lead;
   a sealing plate coupled to the electrical jaw lead, the sealing plate having a stainless steel layer and at least one piezoelectric sensor; and
   an insulative plate disposed between the support base and the sealing plate, wherein the insulative plate is a flex circuit including:
      a plastic substrate; and
      a circuit trace having at least one contact coupled thereto, the at least one contact is coupled to the at least one piezoelectric sensor.

2. The end effector assembly according to claim 1, wherein the contact is configured to operatively couple to a controller via a contact trace.

3. The end effector assembly according to claim 1, wherein the piezoelectric sensor is raised relative to the sealing plate and is configured to create a gap between opposed sealing plates of the jaw members.

4. An electrosurgical instrument for sealing tissue, comprising:
   a housing having at least one shaft that extends therefrom;
   a handle assembly operably coupled to the housing;
   an end effector assembly disposed at a distal end of the at least one shaft including a pair of opposing jaw members, at least one of the jaw members comprising:
      a support base;
      an electrical jaw lead;
      a sealing plate coupled to the electrical jaw lead, the sealing plate having a stainless steel layer and at least one piezoelectric sensor; and
      an insulative plate disposed between the support base and the sealing plate, wherein the insulative plate is a flex circuit including:
         a plastic substrate; and
         a circuit trace having at least one contact coupled thereto, the at least one contact is coupled to the at least one piezoelectric sensor.

5. The electrosurgical instrument according to claim 4, wherein the contact is configured to operatively couple to a controller via a contact trace.

6. The end effector assembly according to claim 4, wherein the piezoelectric sensor is raised relative to the sealing plate and is configured to create a gap between opposed sealing plates of the jaw members.

* * * * *